United States Patent [19]

DeSalva et al.

[11] 3,963,833

[45] June 15, 1976

[54] ANTIPERSPIRANT COMPOSITION AND METHOD CONTAINING A DIHYDRO-BENZOFURAN AND AN ASTRINGENT METAL SALT

[75] Inventors: Salvatore Joseph DeSalva, Somerset; Christopher H. Costello, Millington, both of N.J.

[73] Assignee: Colgate-Palmolive Company, New York, N.Y.

[22] Filed: June 27, 1974

[21] Appl. No.: 483,792

Related U.S. Application Data

[63] Continuation of Ser. No. 262,146, June 2, 1972, which is a continuation-in-part of Ser. No. 106,587, Jan. 14, 1971, Pat. No. 3,775,538.

[52] U.S. Cl. ............................ 424/68; 424/DIG. 5; 424/65; 424/66; 424/67
[51] Int. Cl.$^2$ ...................... A61K 7/34; A61K 7/36; A61K 7/38
[58] Field of Search ................ 424/47, 68, 66, 65, 424/67

[56] References Cited
UNITED STATES PATENTS
3,103,515  9/1963  Zaugg et al. .................... 260/292

*Primary Examiner*—Dale R. Ore
*Attorney, Agent, or Firm*—Norman Blumenkopf; Murray M. Grill; Herbert S. Sylvester

[57] ABSTRACT

The development of perspiration is inhibited by topical application of 3-phenyl-3-carbo-(beta-di-lower alkylamino)-lower alkoxy-2,3-dihydrobenzofuran or a salt thereof, preferably the hydrochloride, and an antiperspirant aluminum, zinc, or zirconium salt, preferably aluminum chlorohydrate or aluminum chloride. The compositions applied may be aqueous, preferably including a surface active agent, such as a nonionic synthetic surface active compound of poly-lower alkylene oxide, or they may be non-aqueous, as in "aerosol" powder sprays. The amounts of the composition employed are small and the proportion of antiperspirant metal salt present is greater than that of the dihydrobenzofuran compound.

16 Claims, No Drawings

ANTIPERSPIRANT COMPOSITION AND METHOD CONTAINING A DIHYDRO-BENZOFURAN AND AN ASTRINGENT METAL SALT

This is a continuation, of application Ser. No. 262,146 filed June 12, 1972 now abandoned which in turn was a continuation-in-part of application Ser. No. 106,587 filed Jan. 14, 1971, now U.S. Pat. No. 3,755,538 issued Nov. 27, 1973.

This invention relates to the inhibition of perspiration, especially from axillary regions, by compositions containing a dihydrobenzofuran compound and an antiperspirant metal salt. More particularly, it relates to antiperspirant compositions comprising 3-phenyl-3-carbo-(di-lower alkylamino)-lower alkoxy-2,3-dihydrobenzofuran or salts thereof, with antiperspirant aluminum, zinc or zirconium salts, and the application of such compositions to the body in areas which perspire.

In accordance with the present invention an antiperspirant composition comprises 3-phenyl-3-carbo-(di-lower alkylamino)-lower alkoxy-2,3-dihydrobenzofuran or a salt thereof or a mixture of such compounds, and an antiperspirant metal salt selected from the group consisting of aluminum, zinc and zirconium salts and mixtures thereof, in which the proportion of the 3-phenyl-3-carbo-(di-lower alkylamino)-lower alkoxy-2,3-dihydrobenzofuran or salt or mixture thereof to the antiperspirant metal salt or mixture thereof is from 1:2 to 1:50. Such compositions are especially effective for counteracting perspiring when they are applied, preferably in aqueous media and with a nonionic surface active agent present, but also in dry aerosol form, to the loci of sweat gland openings in the skin in perspiration-inhibiting amounts. These compositions are rapidly effective, are safe to use, produce no cumulatively adverse effects and result in localized reductions of sweat production and excretion in the area of the body to which they are applied.

The active perspiration-inhibiting compounds of this invention are of two types, the dihydrobenzofuran derivatives and antiperspirant metal salts such as aluminum, zinc, and zirconium. The dihydrobenzofuran compounds are of the formula

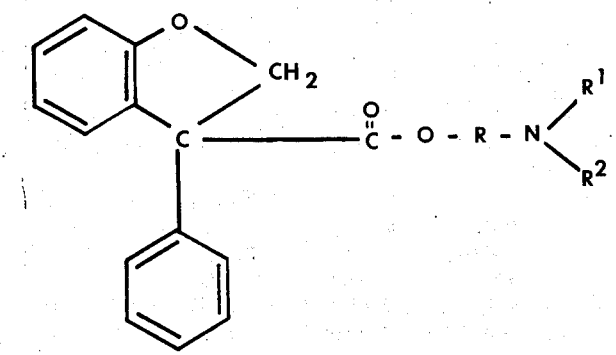

wherein R, $R^1$ and $R^2$ are lower alkyls, usually of 1 to 5 carbons atoms, preferably terminally joined to the O and N, and N atoms, respectively.

Although indicated in the formula in free form, generally the dihydrobenzofuran compounds will be employed as soluble salts, e.g., the hydrochloride. Also, although the dihydrobenzofurans are the most desirable materials employed with the antiperspirant metals salts, in some instances it may be found useful to replace them in part or in whole with the corresponding pyrans, in which the methylene group in the furan ring is replaced with ethylene.

In the most preferred embodiments of the invention R is ethylene. n-Propylene and isopropylene are also acceptable to make an active antiperspirant and often the methylene, butylene and amylene radicals are similarly effective, so that in comparatively broad embodiments of the invention R may be an alkylene of 1 to 5 carbon atoms, straight chained or branched. The $R^1$ and $R^2$ substituents on the amino nitrogen may be any suitable lower alkyls of 1 to 5 carbon atoms but preferably will be of 2 to 3 carbon atoms and most preferably they are both ethyl radicals. It is not required that $R^1$ and $R^2$ be identical although compounds in which they are the same are preferred. $R^1$ and $R^2$ may be conjoined to form a nitrogen-containing ring of 4 to 6 carbon atoms. It is preferred that, in addition to the amino nitrogen, only carbon atoms be in such a ring.

The unsubstituted compounds of the dihydrobenzofuran derivative formula given are preferred but it is within the present invention to substitute for the hydrogen atoms thereof other non-interfering atoms or radicals. Such a substitution will normally be limited to no more than 20% of the hydrogen atoms present, preferably to 10% or fewer thereof. The substitution may be on the aliphatic carbon atoms but it will be more common and more acceptable to substitute on the aromatic carbons. Substituents may be any suitable atoms or radicals which are non-interfering with the antiperspirant activity of the compound, in combination with the antiperspirant metal salt, or, in some cases, they may improve such activity. Among the substituents which may be present are halogens, including bromine, chlorine, iodine and fluorine; nitro; amino; hydroxyl; lower alkyl, especially of 1 to 3 carbon atoms and preferably, ethyl; and lower alkoxy, preferably of 1 to 3 carbon atoms. Normally, there will be no more than two substituents on any aromatic ring R, $R^1$, $R^2$ or —$CH_2$— group. When $R^1$ and $R^2$ are conjoined the limit will be two substituents for the nitrogen-containing ring and preferably, only one. In some preferred embodiments of the invention the unsubstituted or substituted active compounds are salt-forming, preferably of such a type as to be substantially water soluble. Such salts are those of acids, such as the hydrohalic acids, e.g., hydrobromic acid, hydrochloric acid, hydroiodic acid and, in some cases, hydrofluoric acid. Although the hydrohalic acids are preferred salt-forming acids, especially useful with the unsubstituted dihydrobenzofuran compounds, various other well known acids which are capable of forming salts with amines may be utilized, such as sulfuric acid, sulfurous acid, acetic acid, phosphoric acid, boric acid, gluconic, lactic and carbonic acids. Salts resulting from reactions with such acids or similar salt-forming materials will usually be of greater water solubility than the starting active compound and therefore, will be more readily soluble in and compatible with aqueous media usually employed to make the present compositions and for application of the active antiperspirant compounds to the loci of perspiration glands and ducts. Representative of the compounds within the invention that may be employed are the following:

| No. | R | R¹ | R² | Salt-forming acid |
|---|---|---|---|---|
| 1 | ethylene | ethyl | ethyl | HCl |
| 2 | ethylene | ethyl | ethyl | acetic |
| 3 | ethylene | n-propyl | n-propyl | HCl |
| 4 | ethylene | n-propyl | n-propyl | gluconic |
| 5 | ethylene | ethyl | isopropyl | HBr |
| 6 | ethylene | ethyl | isopropyl | HCl |
| 7 | n-propylene | ethyl | ethyl | HCl |
| 8 | n-propylene | ethyl | ethyl | carbonic |
| 9 | isopropylene | isopropyl | isopropyl | HI |
| 10 | isopropylene | isopropyl | isopropyl | HCl |
| 11 | n-amylene | ethyl | n-amyl | $H_3PO_3$ |
| 12 | n-amylene | ethyl | n-amyl | $HNO_3$ |
| 13 | ethylene | n-amyl | n-amyl | HCl |
| 14 | ethylene | n-amyl | n-amyl | $H_2SO_4$ |
| 15 | ethylene | methyl | methyl | HCl |
| 16 | ethylene | ethyl | methyl | HBr |
| 17 | ethylene | ethyl | ethyl | — |
| 18 | isopropylene | isopropyl | isopropyl | — |
| 19 | ethylene | ethyl | ethyl | lactic |

The various antiperspirant or astringent metal salts known in the cosmetic art to be useful for inhibiting the development of perspiration on the human body may be included with the present dihydrobenzofuran compounds in the improved antiperspirant compositions of this invention. Of such salts, those of aluminum, zinc and zirconium are considered to be most useful and to result in the most improved combinations of ingredients with the dihydrobenzofuran compounds, combinations which have significantly better anhidrotic effects. The preferred antiperspirant salts are aluminum chlorohydrates and aluminum chloride, although other aluminum salts such as aluminum sulfate, aluminum sulfamate, aluminum sulfonate, and aluminum salts of higher alkyl benzene sulfonic acids may also be used. Zirconium salts, such as zirconium chloride, zirconium oxychlorides and zirconium sulfate are also useful. Also, zinc salts such as zinc phenolsulfonate, zinc sulfate, zinc chloride, and alkaline earth metal chlorides and sulfates are also useful astringents and the alkaline earth metal salts may be employed in replacement of a part of the aluminum, zinc or zirconium salts, generally to an extent of less than 30% thereof.

Most of the active antiperspirant compounds of the dihydrobenzofuran compound and antiperspirant metal salt types are usually best applied to the skin from cosmetic preparations in solution, emulsion, paste, galatinous, spray, aerosol, powder or other suitable form and media. Often, aqueous or alcoholic media are used and the physical forms of the cosmetics assist in applying the active material topically to the locus where perspiration is generated. Various vehicles may be utilized other than water and ethanol and mixtures thereof including the water soluble monohydric and polyhydric alcohols, e.g., alcohols of 1 to 6 carbon atoms and 1 to 5 hydroxyls, such as ethanol, propanol, isopropanol, glycerol, sorbitol, ethylene glycol, propylene glycol, poly-lower alkylene glycols, such as polyethylene glycol (Carbonwaxes of molecular weights from 300 to 10,000); monoglycerides in which the fatty acid component is of 12 to 18 carbon atoms; e.g., glyceryl monolaurate; plus other materials to improve various properties of the cosmetic preparations. In one of such uses the described dihydrobenzofuran compound will be present in a non-aqueous liquefied gas propellant medium to be dispensed as a dry powder onto the skin. In some cases the active ingredients may be used without additional cosmetic, emulsifier or "aesthetic" agents but generally such will be present to make the product more attractive and more acceptable to the consumer.

To assist the present actively anhidrotic compounds to contact and "penetrate" the skin at the sites of sweat glands or ducts, it is desirable for a wetting agent to be present. Of such compounds, the nonionics are considered to be best, although in many applications other surface active compounds, which may be amphoteric, anionic or cationic, are also useful.

A preferred nonionic surface active agent is of the type sold under the trade name Pluronic, a block copolymer which is a condensation product of ethylene oxide with a hydrophobic base portion obtained by condensing propylene oxide with propylene glycol. Various Pluronics are suitable, including those identified as L61, L64 and F68, with the last mentioned often being preferred. The molecular weights of such and similar condensation products of lower alkylene oxide with a lower alkylene oxide-lower alkylene glycol hydrophobic base are usually from about 2,000 to 20,000 and the lower alkylenes are of 2 to 4 carbon atoms, with those of three or four carbon atoms being used to make the hydrophobic portion of the molecule, which generally has a molecular weight of from about 1,200 to 2,500, preferably 1,500 to 1,800. The ethylene oxide content of the nonionics (Pluronics, etc.) is usually from 65 to 85%.

Other nonionic surface active agents that are useful in the practice of the present invention include the condensation products of lower alkylene oxides, which are hydrophilic, with organic hydrophobes, either aliphatic or aromatic. Such compounds include detergents that are polyalkylene glycol esters, ethers or thioethers, wherein the hydrophobic portions of the molecules contain from about 8 to 18 carbon atoms and the number of alkylene oxides, almost always ethylene oxide, is from about 3 to 50. The hydrophobic groups may be long chain fatty alcohols or acids of 8 to 18 carbon atoms, or alkyl phenols or alkyl thiophenols in which the alkyl groups are of 6 to 12 carbon atoms, preferably eight or nine carbon atoms, either straight chained or branched. Also useful are the tertiary trialkyl amine oxides wherein one alkyl has 10 to 18 carbon atoms and the other two are of 1 to 3 carbon atoms. Specific examples of such useful nonionic surface active agents include lauryl polyethoxy ethanol wherein there are present 20 moles of ethylene oxide per mole of fatty alcohol, nonyl phenol polyethoxyethanol having 15 moles of ethylene oxide per mole and dodecyl dimethylamine oxide.

In addition to or in replacement of the nonionic surface active agents, amphoteric compounds such as the alkyl beta-amino dipropionates, imidazoline compounds of the Miranol type and alkyl beta-amino propionates, the alkyl groups of which compounds are of 8 to 14 carbon atoms, are also useful. The cationic surface active agents which are also useful include quaternary ammonium salts wherein one or two of the substituents on the quaternary nitrogen are hydrophobic "long chain" radicals and two or three are short chain alkyls, with the salt-forming ion being any suitable such ion, such as halide, including chloride, iodide and bromide, phosphates, nitrate, methosulfate, sulfate or sulfonate. Generally the hydrophobic substituents will contain from 8 to 25 carbon atoms, either as aliphatic or aliphaticaromatic radicals, e.g., alkyl or alkyl benzene. Specific examples of quaternary compounds are cetyl trimethyl ammonium bromide, benzethonium chloride, N-cetyl pyridinium bromide, and dodecyl dimethyl benzyl ammonium chloride.

Among the anionic surface active agents that are useful there may be mentioned the sulfated and sulfonated synthetic organic detergents, such as the higher alkyl sulfates; the higher alkyl aromatic sulfonates; the sulfonated amides of higher fatty acids; the higher fatty acid monoglyceride sulfates; the higher alkyl poly-lower alkoxy ether sulfates and sulfonates; the higher olefin sulfontes; and the mono and di-higher alkyl sulfosuccinates. The salt-forming ions will preferably be sodium, potassium, ammonium or lower alkanolammonium. The alkyls will usually be of 8 to 18 carbon atoms and the lower alkoxides will be of 2 to 3 carbon atoms, preferably two carbon atoms. Specific examples of such materials which may be employed include: sodium lauryl sulfate; sodium n-octadecyl sulfate; monoethanolammonium pentadecyl sulfate; diethanolammonium oleyl sulfate; sodium dioctyl sulfosuccinate; sodium nonyl benzene sulfonate, potassium pentadecyl benzene sulfonate; sodium tridecyl benzene sulfonate; sodium salt of the lauric acid amide of taurine; sodium coconut oil monoglyceride sulfate; sodium N-lauroyl sarcoside; and the potassium salt of the oleic acid ester of isethionic acid. The polyalkoxy groups are of 3 to 50 per mole of compound. Also useful are the higher fatty acid (10 to 18 carbon atoms) soaps, such as those made from mixtures of coconut oil and tallow, saponified by sodium hydroxide or potassium hydroxide.

Although the various vehicles and surface active agents improve the ability of the active ingredient to contact the entire surface of the skin to which it is is applied and thereby help make it more effective, they also often facilitate production of a composition containing the antiperspirant compound in a cosmetically desirable physical state for application by the user. Solutions, emulsions, gels, powders, sprays, including aerosols, may be made from the active ingredients alone or with carriers, emulsifiers or dispersants, including solvents. Usually, however, various adjuvants will also be present, either to improve the appearance, physical characteristics or cosmetic acceptability of the product or to give it other desirable properties. Thus, among such adjuvants are: thickening agents, e.g., hydroxypropyl methyl cellulose, polyvinyl pyrrolidone polyvinyl alcohol, sodium carboxymethyl cellulose; humectants, e.g., glycerol, propylene glycol; other emulsifiers; pH-regulating agents, such as salts of weak acids and strong bases or strong acids and weak bases, e.g., sodium acetate, borates; perfumes, dyes; pigments, preferably water dispersible; carriers, e.g., talc, pyrogenic silicas, diatomaceous earth; sequestrants, e.g., trisodium nitrilotriacetate, tetrasodium ethylene diamine tetraacetate; fatty materials and oils, e.g., paraffin, petrolatum monoglycerides, diglycerides, stearic acid; propellants, e.g., Propellants 11, 12, 114; bactericides, e.g., hexachlorophene; fungicides; and antibiotics, e.g., neomycin.

To make the compositions and methods of the present invention effective it is important that the ratio of dihydrobenzofuran compound to antiperspirant metal salt be such that the major proportion of such combination is of the metal salt. The ratio should be from 1:2 to 1:50, preferably from 1:4 to 1:20, of dihydrobenzofuran compound:antiperspirant metal salt, with a most preferred range being about 1:8 to 1:12. Such ratios are by weight, as are other ratios, amounts and percentages given herein. When the proportion of dihydrobenzofuran compound is increased beyond the limits given, the advantages of the improved effect due to the presence of the antiperspirant metal salt are less and when the proportion of the antiperspirant metal salt is greater than indicated, the effects may be essentially the same as those of the antiperspirant metal salt alone. In both such cases the results are usually considered to be less satisfactory than those obtained from the mentioned proportions of the antiperspirant ingredients.

The proportion of the total combined contents of the dihydrobenzofuran compound and antiperspirant metal salts in the present compositions may be adjusted to fit the particular type of material being utilized but will generally be in the 1 to 50% range, preferably 2 to 20% and most preferably 2 to 10%. The balance of such compositions may be any suitable cosmetic base or antiperspirant composition base, which may contain other active ingredients. Thus, lotions and creams, as well as gels, solids (sticks), solutions, sprays, powders and foams, may be employed. The bases for such compositions may be primarily water; alcohol; aqueous alcoholic solvents; emulsified higher fatty acids, e.g., stearic acid; cosmetic bases, including petrolatum, spermaceti; higher fatty acid monoglycerides, e.g., coconut oil fatty acid monoglyceride; the corresponding diglycerides; natural animal fats and vegetable oils; halogenated lower hydrocarbon propellants; or may be extracts of various plants. In most cases it is desirable for the aqueous, aqueous alcoholic or non-aqueous solvent or propellant content thereof to be a major proportion of the product. Of course, when dry powders are being dispensed, as from aerosol compositions, the moisture content may be much lower or will be neglible in most cases. Such compositions utilize the well known liquefied gases, such as Propellants 12, 114, and 121 or propane and isobutane to force the powdered active ingredients out through a dispensing valve onto the locus to be treated. However, for aqueous or aqueous-alcoholic compositions, the proportion of moisture present may be a major proportion and often is at least 20%, e.g., 20 to 98%.

In the compositions of this invention the content of dihydrobenzofuran compound, preferably as a hydrochloride, is often from 0.02 to 2% and the content of antiperspirant metal salt, such as aluminum chlorohydrate or aluminum chloride is from 1 to 20%, with preferred ranges being 0.1 to 1% and 1 to 10%, respectively. In highly preferred proportions the quantity of dihydrobenzofuran compound is from 0.1 to 0.5% and that of the antiperspirant aluminum salt is from 2 to 5%, when dispensed in aqueous media or from aerosols. However, when mixtures of solids are employed the proportions may be much greater, even totaling 100%. Talc or similar water insoluble or soluble powder may be utilized as a carrier for the solids or powdered products.

The surface active agent in the preferred compositions, preferably a nonionic detergent material, will generally be from 0.2 to 10 or 20% of the composition, preferably from 0.5 to 5% thereof. Utilizing such proportions in the finished aqueous product, a desired wetting effect is obtained and the amount of wetting agent present is not so great as to make the composition unduly sticky or otherwise objectionable. Other compounds may be included, with the proportions thereof generally being from 0.1 to 25%, preferably from 0.1 to 15%. Of course, such adjuvants will be chosen to be compatible with the active anhidrotic compounds present under the usual storage conditions. Because the antiperspirant metal salts are generally most effective in somewhat acidic environments the pH of the aqueous products will usually be from 3 to 6, preferbly 4 to 5. Buffers may be employed to maintain the pH in such ranges but are not usually requied.

The amounts of the mentioned compositions which are applied to the body at any one time will desirably be such as to deposit evenly on the locus to be treated, usually the human axillae, from 0.5 to 10 milligrams of the dihydrobenzofuran compound, preferably from 1 to 5 mg. thereof, and from 5 to 50 mg. of antiperspirant metal salt, preferably from 10 to 25 mg. thereof, to each of the axillae, often with 0.2 to 20 mg. nonionic.

The application of anhidrotic or antiperspirant composition used will be normally made to the locus to be treated at room temperature, preferably from a roll-on applicator or by dabbing or padding the skin when the composition is an aqueous or an aqueous alcoholic solution. Alternatively, the composition may be applied as a cream or lotion, an aerosol spray, liquid or powder, or as an "antiperspirant talcum powder". Such application may be effected once a day although up to three such applications per day, in case of a severe problem, may be desired.

After application of compositions containing the dihydrobenzofuran compound and the antipersirant metal salt diminution of excretion of perspiration is noted. Generally, this diminution is apparent a short time after application, usually within 15 minutes to three hours. The anhidrotic effect gradually increases to a maximum, which is followed by a gradual diminution of activity. After about 20 to 24 hours, little effect will usually be observed. When the antiperspirant compositions containing dihydrobenzofuran compound and antiperspirant metal salt are applied daily the anhidrotic action is maintained. The decreases perspiration rate is noted by most subjects employing the present compositions and the superiority thereof compared to control antiperspirant metal salt compositions and dihydrobenzofuran compounds alone is definitely established. Such results are verified in animal tests wherein sweating is stimulated by application of pilocarpine or electrical shock to the loci of the sweat glands and ducts, e.g., those in a cat's paw, and such loci are then topically or subcutaneously treated with the invention or control compositions. By these methods the significant effectiveness and improved anhidrotic results attending the use of the present anhidrotic compositions and processes are shown and they are supported by panel tests performed on adult human subjects.

The present invention results in several significant advantages and allows the production of antiperspirant compositions which are superior in various respects to those presently on the market and to those based on the particular dihydrobenzofuran compounds alone. The lesser amounts of the heavy metal salts used make the present compositions feel less sticky, not as "heavy" and less drying to the skin. Anhidrotic effects are improved, and the compositions are decidedly effective, both on the first day of use and after a number of days of continuous use.

The following examples illustrate various embodiments of the invention and should not be considered to be limitative of the above invention. Unless otherwise indicated all parts are by weight and all temperatures are in °C.

EXAMPLE 1

|  | Parts |
|---|---|
| 3-Phenyl-3-carbo-(beta-diethylamino)-ethoxy-2,3-dihydrobenzofuran hydrochloride | 0.25 |
| *Aluminum chlorohydrate | 2.5 |
| **Nonionic surface active agent | 1.0 |
| Water, deionized | 96.25 |
|  | 100.00 |

*$Al_2(OH)_5Cl.2H_2O$, impalpable powder
**Pluronic F-68 (block copolymer of ethylene oxide with reaction product of propylene glycol and propylene oxide, molecular weight of about 8,700, mfd. by Wyandotte Chemicals Corporation)

A product of the above formula is made by mixing the nonionic surface active agent with the water and then adding to this the dihydrobenzofuran compound hydrochloride and aluminum chlorohydrate.

The composition is tested on a panel of subjects, with each subject applying one milliliter of the aqueous solution to one axilla daily for a period of 5 days, followed by a rest period of no treatment for two days, after which the five day treatment is repeated. During the periods of treatment the amounts of perspiration developed are measured and compared to the perspiration of the other of each of the subjects' axillae and a previous "perspiration rate" developed for each of the panel members. In some cases the amount of perspiration is reduced to about 60 to 75% of that which would be expected to be exuded at the normal rate of perspiring. The mean maximal daily anhidrosis for the panel is 37%. None of the subjects treated experiences any adverse effects, such as irritation, allergic reactions, pain or discomfort. In a similar experiment, in which the procedure described is followed except for the employment of aluminum chloride instead of aluminum chlorohydrate the results obtained are essentially the same, with a slightly lower mean maximal daily anhidrosis but with such result being over 30%.

When, instead of either the aluminum chlorohydrate or aluminum chloride there is substituted aluminum sulfate, aluminum sulfamate, zinc phenolsulfonate, zinc sulfate, zirconium oxychloride, zirconium chloride, zirconium sulfate or when there is substituted for 25% of the aluminum chlorohydrate, zinc phenolsulfonate or zinc sulfate, an alkaline earth metal chloride, e.g., calcium chloride, the improvement in anhidrotic activity noted with the compositions also containing the mentioned dihydrobenzofuran compound also occurs. Similarly, when in any of such compositions, the dihydrobenzofuran compound is replaced by the corresponding 3-phenyl-3-carbo-(beta-diethylamino)-ethoxy-2,3-dihydrobenzofuran, the corresponding hydrobromide, sulfate, or nitrate salt, or when the dihydrobenzofuran compound is modified to change the ethylene group thereof to propylene or methylene and to change the ethyl groups thereof to other lower alkyls, including methyl, isopropyl and n-butyl, improved anhidrotic effects are obtained, compared to separate uses of the mentioned antiperspirant materials. This is also the case when in any of the combination formulas mentioned, the Pluronic F-68 is replaced with Pluronic L-61 or Pluronic L-64 or with other nonionic surface active agents, such as Igepal CO-630, polyethoxylated higher fatty alcohols, higher fatty acid esters of polyethoxy ethanols and corresponding higher fatty ethers of poly-lower alkoxy-lower alkanols.

The proportions of the dihydrobenzofuran compound and antiperspirant metal salt described previously in this Example are modified with respect to each of the compositions so as to be 1:20; 1:4 and 1:2. All such compositions, when applied to the axillae at a rate equivalent to 12, 28 and 55 mg. active antiperspirants per axilla are effective anhidrotic compositions, superior in anhidrotic activity to larger amounts of each of the constituents alone. Such is also the case when the compositions are in aqueous alcoholic solution, in lotions, gels, creams and sprays, and when they are sprayed from an aerosol container as mixed powders on a base of 90% of talc or pyrogenic silica.

EXAMPLE 2

Utilizing the same quantities of materials as described in Example 1, (1 milliliter per axilla of an aqueous solution containing 0.25% of dihydrobenzofuran compound, 2.5% of aluminum chlorohydrate and 1% of Pluronic F-68) but with the anhidrotic ingredients kept apart, so that two solutions are employed, (A) 0.25 part of dihydrobenzofuran compound hydrochloride, 0.5 part nonionic surfactant and 49.25 parts of water; and (B) 2.5 parts aluminum chlorohydrate, 0.5 part nonionic surfactant and 47 parts water, the liquid solutions are applied at the same time to the axilla to be treated. It is found that no substantial difference in anhidrotic effect results between the treatments of Examples 1 and 2.

EXAMPLE 3

A series of animal experiments is conducted, employing the cat-paw perspiration technique, to determine the comparative effectivenesses of compositions of this invention at different ratios of the dihydrobenzofuran compound and antiperspirant metal salt. In the experiments, perspiration of a cat's paw is artificially stimulated by pilocarpine injections and the paw is then topically treated with compositions of this invention and the amount of perspiration developed is measured. Various combinations of 3-phenyl-3-carbo-(beta-diethylamino)-ethoxy-2,3-dihydrobenzofuran hydrochloride and either $Al_2(OH)_5Cl.2H_2O$ or $AlCl_3$ are tested at application rates of 0.1 to 3.2 mg. of the dihydrobenzofuran compound, one to eight mg. of aluminum chloride and one to sixteen mg. of aluminum chlorohydrate, and comparisons are made between the anhidrotic effects of such compositions and those of the individual constituents. It is found that, as reported in Example 1, the aluminum chlorohydrate-dihydrobenzofuran derivative combination is superior in anhidrotic effects to the aluminum chloride-dihydrobenzofuran derivative combination with respect to effective antiperspirant activity. Greatest activities are obtained at the greatest concentrations of the dihydrobenzofuran derivative and aluminum salts and preferably from 3 to 10 times as much aluminum chlorohydrate as dihydrobenzofuran derivative is used and from 5 to 20 times as much of the aluminum chloride with such derivative. The invented compositions are significantly more anhidrotic than compositions containing more of one such anhidrotic component.

EXAMPLE 4

The formulations of Example 1 are filled into collapsible compartments in pressurized containers, so that upon depressing of the valve buttons, fine aqueous sprays of the antiperspirant composition solutions are dispensed, which may be directed onto the axillae. Using such dispensing method and the described compositions a "warm" spray is obtained which does not drip excessively when applied in the described quantity nor does the spray "bounce off" the axillae to be lost. Desirable pressures are from 5 to 40 lbs./sq. in. The combination compositions of the invention are found to be highly successful as antiperspirants, as described in Example 1.

EXAMPLE 5

Various cosmetic bases known in the art to be useful for application of antiperspirant compositions in spray, liquid, cream, roll-on, lotion, stick or pad form are prepared and to each is added sufficient dihydrobenzofuran derivative of Example 1, as the hydrochloride, to result in the application of 0.1 to 3.2 mg. of such compound per milliliter of product, together with about four times as much of the aluminum chlorohydrate in the one case and six times as much aluminum chloride in the other. In such instances improved antiperspirant activity is obtained over double the contents of either the dihydrobenzofuran derivative or the aluminum salts. See Sagarin, *Cosmetics:Science and Technology* (1957) or other cosmetic tests for useful formulas of the cosmetic bases which are used.

EXAMPLE 6

An aerosol powder spray composition is prepared of the formula:

| | Parts |
|---|---|
| 3-Phenyl-3-carbo-(beta-diethylamino)-alkoxy-2,3-dihydrobenzofuran | 0.4 |
| Aluminum chlorohydrate, impalpable (Reheis Chemical Company) | 3.0 |
| Pyrogenic silica (Cab-O-Sil M-5, Cabot Corporation) | 0.5 |
| *Vehicle | 4.0 |
| Perfume | 0.3 |
| Propellant mixture (60 parts Propellant 11: 40 parts Propellant 12) | 91.8 |

*Isopropyl myristate, coconut oil monoglyceride, coconut oil diglyceride, or 1:1 Pluronic L-44:F-68 mixture (ethylene oxide-propylene oxide block copolymers)

An aerosol dispenser is filled with the above composition in a normal manner, with the propellant gas being added last under pressure. To use it the anhydrous product is dispensed directly onto the axillae at the rate of about 1 ml./axilla. Improved antiperspirant activity is noted shortly after application compared to the same compositions containing larger proportions of either the dihydrobenzofuran compound or the aluminum chlorohydrate, alone.

The invention has been described with respect to examples and illustrations thereof but is not to be limited to these inasmuch as it will be evident to one of skill in the art that modifications thereof may be made and equivalents may be substituted without departing from its scope.

What is claimed is:

1. An antiperspirant composition comprising 3-phenyl-3-carbo-(di-lower alkylamino)-lower alkoxy-2,3- dihydrobenzofuran or a salt thereof selected from the group consisting of hydrohalic, sulfuric, sulfurous, acetic, phosphoric, boric, nitric, lactic, gluconic, and carbonic acid salts and mixtures thereof, and an antiperspirant metal salt selected from the group consisting of aluminum chlorhydrate, aluminum chloride, aluminum sulfate, aluminum sulfamate, aluminum sulfonate, zinc phenolsulfonate, zinc sulfate, zinc chloride, zirconium oxychloride, zirconium chloride, zirconium sulfate, alkaline earth metal chloride, and alkaline earth metal sulfate and mixtures thereof, in which the proportion of the 3-phenyl-3-carbo-(di-lower alkylamino)-lower alkoxy-2,3-dihydrobenzofuran compound to the antiperspirant metal salt is from 1:2 to 1:50 and wherein the total of said dihydrobenzofuran compound and said antiperspirant metal salt in the composition is from 1 to 50%, and the balance being a cosmetic vehicle.

2. An antiperspirant composition according to claim 1 wherein the dihydrobenzofuran compound is a 3-phenyl-3-carbo(beta-diethylamino)-ethoxy-2,3-dihydrobenzofuran salt, the ratio of the dihydrobenzofuran compound salt to antiperspirant metal salt is in the range of 1:4 to 1:20 and the total content of such compounds in the composition is from 2 to 10%.

3. An antiperspirant composition according to claim 2 wherein the dihydrobenzofuran compound salt is 3-phenyl-3-carbo-(beta-diethylamino)-ethoxy-2,3-dihydrobenzofuran hydrochloride and the antiperspirant metal salt is $Al_2(OH)_5Cl.2H_2O$.

4. An antiperspirant composition according to claim 2 wherein the dihydrobenzofuran compound salt is 3-phenyl-3-carbo-(beta-diethylamino)-ethoxy-2,3-dihydrobenzofuran hydrochloride and the antiperspirant metal salt is $AlCl_3$.

5. An antiperspirant composition according to claim 2 wherein the dihydrobenzofuran compound salt is a hydrochloride the amount of dihydrobenzofuran compound hydrochloride is from 0.02 to 2% and the amount of antiperspirant salt is from 1 to 20%.

6. An antiperspirant composition according to claim 5 wherein the antiperspirant composition is a solution of the dihydrobenzofuran compound hydrochloride and the antiperspirant salt, which also contains from 0.2 to 10% of nonionic synthetic organic surface active agent.

7. An antiperspirant composition according to claim 6 wherein the antiperspirant salt is $Al_2(OH)_5Cl.2H_2O$ and the nonionic surface active agent is a block copolymer of ethylene oxide and propylene oxide of a molecular weight of 2,000 to 20,000 and in which the content of ethylene oxide is about 65 to 85%.

8. An antiperspirant composition according to claim 6 wherein the antiperspirant salt is $AlCl_3$ and the nonionic surface active agent is a block copolymer of ethylene oxide and propylene oxide of a molecular weight of 2,000 to 20,000 and in which the content of ethylene oxide is about 65 to 85%.

9. An antiperspirant composition according to claim 1 wherein the cosmetic vehicle is water.

10. A method for inhibiting perspiration which comprises applying to the locus of sweat gland openings on the skin an effective perspiration-inhibiting amount of an antiperspirant composition comprising from 0.02 to 2 percent by weight of 3-phenyl-3-carbo-(di-lower alkylamino)-lower alkoxy-2,3-dihydrobenzofuran or a salt thereof selected from the group consisting of hydrohalic, sulfuric, sulfurous, acetic, phosphoric, boric, nitric, lactic, gluconic, and carbonic acid salts and mixtures thereof, and from 1 to 20 percent by weight of a salt salt selected from the group consisting of aluminum chlorhydrate, aluminum chloride, aluminum sulfate, aluminum sulfamate, aluminum sulfonate zinc phenolsulfonate, zinc sulfate, zinc chloride, zirconium oxychloride, zirconium chloride, zirconium sulfate, alkaline earth metal chloride, and alkaline earth metal sulfate and mixtures thereof and the balance being a cosmetic vehicle.

11. A method according to claim 10 wherein the antiperspirant composition applied is one wherein the dihydrobenzofuran compound is a 3-phenyl-3-carbo-(beta-diethylamino)-ethoxy-2,3-dihydrobenzofuran salt and the antiperspirant metal salt is selected from the group consisting of aluminum chlorohydrate, aluminum chloride, aluminum sulfate, zinc phenolsulfonate, zinc sulfate, zinc chloride, zirconium oxychloride, zirconium chloride and zirconium sulfate.

12. A method according to claim 11 wherein the dihydrobenzofuran compound is 3-phenyl-3-carbo-(beta-diethylamino)-ethoxy-2,3-dihydrobenzofuran hydrochloride and the amount of the antiperspirant composition applied to each axilla is that which contains from 5 to 50 milligrams of antiperspirant metal salt and 0.5 to 10 milligrams of the dihydrobenzofuran compound hydrochloride.

13. A method according to claim 12 wherein there is applied to each of the axilla, as a part of the antiperspirant composition, from 0.2 to 20 milligrams of nonionic surface active agent in water.

14. A method according to claim 13 wherein the nonionic surface active agent is a block copolymer of ethylene oxide and propylene oxide having a molecular weight of 2,000 to 20,000 and an ethylene oxide content of 65 to 85%.

15. A method according to claim 14 wherein the antiperspirant metal salt is $Al_2(OH)_5Cl.2H_2O$.

16. A method according to claim 2 wherein the antiperspirant metal salt is $AlCl_3$.

* * * * *